US009011775B2

(12) United States Patent
McMennamy et al.

(10) Patent No.: US 9,011,775 B2
(45) Date of Patent: Apr. 21, 2015

(54) CATION EXCHANGE CAPACITY TITRATION UNIT

(75) Inventors: George McMennamy, Richmond, TX (US); Marian Baranowski, Houston, TX (US); Arkadiy Belkin, Houston, TX (US)

(73) Assignee: M-I L.L.C., Houston, TX (US)

( * ) Notice: Subject to any disclaimer, the term of this patent is extended or adjusted under 35 U.S.C. 154(b) by 637 days.

(21) Appl. No.: 13/145,457

(22) PCT Filed: Jan. 25, 2010

(86) PCT No.: PCT/US2010/021991
§ 371 (c)(1),
(2), (4) Date: Jul. 20, 2011

(87) PCT Pub. No.: WO2010/085750
PCT Pub. Date: Jul. 29, 2010

(65) Prior Publication Data
US 2011/0281370 A1    Nov. 17, 2011

Related U.S. Application Data

(60) Provisional application No. 61/147,416, filed on Jan. 26, 2009.

(51) Int. Cl.
*G01N 31/00* (2006.01)
*G01N 31/16* (2006.01)
(Continued)

(52) U.S. Cl.
CPC ............... *G01N 31/16* (2013.01); *G01N 33/24* (2013.01); *G01N 21/79* (2013.01)

(58) Field of Classification Search
CPC .......... G01N 31/00; G01N 31/16; A61K 6/00

USPC ............................................ 422/68, 500–503
See application file for complete search history.

(56) References Cited

U.S. PATENT DOCUMENTS 4,003,705 A * 1/1977 Buzza et al. .................... 436/68
4,403,866 A   9/1983 Falcoff et al.
(Continued)

FOREIGN PATENT DOCUMENTS

| JP | 55-154452 | 12/1980 |
| JP | 04-127058 | 4/1992 |
| WO | 00/19194 A1 | 4/2000 |
| WO | 2005/003754 A2 | 1/2005 |

OTHER PUBLICATIONS

Office Action to Mexican Patent Application No. MX/a/2011/007851 dated Oct. 15, 2013.
(Continued)

*Primary Examiner* — Sally Merkling

(57) ABSTRACT

Disclosed herein is a cation exchange capacity titration unit comprising a titration cell having a closed bottom end in fluid communication with an open top end; a recirculation loop comprising a pump and a sensing unit, wherein the pump comprises a pump inlet in fluid communication with the bottom end of the titration cell, and a pump outlet in fluid communication with a sensing unit inlet, the sensing unit inlet being in fluid communication with a sensing unit outlet, wherein the sensing unit outlet is in fluid communication with the top end of the titration cell such that operation of the pump results in an analyte sample flowing from the bottom end through the pump, through the sensing unit, and back into the top end of the titration cell in a continuous loop. A method of determining the cation exchange capacity of a sample is also disclosed.

6 Claims, 2 Drawing Sheets

(51) Int. Cl.
*G01N 21/79* (2006.01)
*G01N 33/24* (2006.01)

(56) References Cited

U.S. PATENT DOCUMENTS

| | | | |
|---|---|---|---|
| 5,924,794 A * | 7/1999 | O'Dougherty et al. | ....... 366/136 |
| 6,146,008 A | 11/2000 | Laederich et al. | |
| 6,582,663 B1 | 6/2003 | Schulz et al. | |
| 2004/0058451 A1 | 3/2004 | Pauli et al. | |

OTHER PUBLICATIONS

International Search Report and Written Opinion for PCT/US2010/021991.

G. Kahr et al, "Determination of the Cation Exchange Capacity and the Surface Area of Bentonite, Illite and Kaolinite by Methylene Blue Adsorption", Applied Clay Science, vol. 9, No. 5, (Feb. 1, 1995), pp. 327-336.

* cited by examiner

CATION EXCHANGE CAPACITY TITRATION UNIT

BACKGROUND OF INVENTION

1. Field of the Invention

This invention relates to a cation exchange capacity titration unit and a method of determining the cation exchange capacity of drilled solids. More particularly, an automated cation exchange capacity titration unit and a method of determining the cation exchange capacity of drilled solids using the automated cation exchange capacity titration unit described herein.

2. Background Art

The cation exchange capacity of a drilling fluid, also referred to in the art as the methylene blue capacity, is an important consideration when drilling and/or servicing a well. The cation exchange capacity of a drilling fluid is typically determined utilizing a titration method similar to method API 13B-1 or equivalent. The cation exchange capacity of a drilling fluid is an indication of the amount of reactive clays (e.g., bentonite and/or drill solids) present as determined by the methylene blue test. The methylene blue capacity provides an estimate of the total cation exchange capacity of the drilling fluid solids. Methylene blue capacity and cation exchange capacity may not necessarily be equivalent, the former normally being somewhat less than the actual cation exchange capacity.

To determine the methylene blue capacity of a sample, a methylene blue solution is added to a sample of drilled solids which has first been treated with hydrogen peroxide and acidified to remove organic matter. The sample is titrated with methylene blue until the sample suspension is saturated with methylene blue, as determined by the presence of a dye 'halo' around a drop of the titrated suspension placed on a piece of filter paper. Variations of the procedure may be used on drill solids and/or on samples of commercial bentonite and/or other clays to allow an estimate of the amount of each type of solid present in a particular fluid.

However, this procedure is time intensive and the results may be operator dependent. A need exists for determining the cation exchange capacity of a sample in a more automated way, wherein the results are less subjective than allowed for utilizing the methods currently known in the art.

SUMMARY OF INVENTION

In a first aspect of the present invention, a cation exchange capacity titration unit comprises:

a titration cell having a closed bottom end in fluid communication with an open top end;

a recirculation loop comprising a pump and a sensing unit, wherein the pump comprises a pump inlet in fluid communication with the bottom end of the titration cell, and a pump outlet in fluid communication with a sensing unit inlet, the sensing unit inlet being in fluid communication with a sensing unit outlet, wherein the sensing unit outlet is in fluid communication with the top end of the titration cell such that operation of the pump results in an analyte sample flowing from the bottom end through the pump, through the sensing unit, and back into the top end of the titration cell in a continuous loop;

the sensing unit further comprising a sensing element capable of providing a signal proportional to a concentration of an analyte in the liquid analyte sample;

the titration unit further comprising a dispensing burette capable of dispensing a known amount of a titrant into the top end of the titration cell.

In another aspect of the present invention, a cation exchange capacity titration unit comprises:

a titration cell, a metering pump, and a data acquisition computer control system;

the titration cell having a closed bottom end in fluid communication with an open top end;

a recirculation loop capable of circulating a liquid analyte sample from the bottom end of the titration cell back into the top end of the titration cell, the recirculation loop comprising a pump and a sensing unit, wherein the pump comprises a pump inlet in fluid communication with the bottom end of the titration cell, and a pump outlet in fluid communication with a sensing unit inlet, the sensing unit inlet being in fluid communication with a sensing unit outlet, wherein the sensing unit outlet is in fluid communication with the top end of the titration cell;

the sensing unit further comprising a sensing element capable of providing an output signal proportional to a concentration of an analyte in the liquid analyte sample;

the metering pump having an inlet in fluid communication with a titrant reservoir, and a dispensing outlet in fluid communication with the top end of the titration cell, wherein the metering pump is capable of dispensing a known amount of a titrant from the titrant reservoir into the titration cell in response to an output from the computer control system;

the computer control system comprising a sensor input in electronic communication with the sensing unit, a metering pump output in electronic communication with the metering pump, a central processor, a data storage system, an operator interface, and a data manipulation system, wherein the computer control system is capable of transferring inputs and/or outputs to and from the computer control system to the sensing unit and/or the metering pump, and wherein the computer control system is capable of accepting input from and displaying information to an operations technician, to determine the cation exchange capacity of a sample.

In still another aspect of the present invention, a method of determining the cation exchange capacity of a sample comprises the steps of: disposing an amount of a sample into the titration cell of the herein described cation exchange capacity titration unit, diluting the sample with a known volume of water; engaging the pump such that the sample circulates in the recirculation loop from the bottom end of the titration cell back into the top end of the titration cell, titrating the sample by contacting the sample with portions of the titrant in the titration cell utilizing the dispensing burette and recording the output of the sensing element in response to the addition of the titrant until an end point in the titration is reached, wherein the titrant comprises methylene blue.

These and other features, aspects and advantages of the present invention will become better understood with reference to the following drawings, description and claims.

DETAILED DESCRIPTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

In the following description, numerous specific details are set forth to provide a thorough understanding of the present invention. However, it will be obvious to those skilled in the art that the present invention may be practiced without such specific details. In other instances, well-known devices have been shown in block diagram form in order not to obscure the present invention in unnecessary detail. For the most part, details unnecessary to obtain a complete understanding of the present invention have been omitted in as much as such details are within the skills of persons of ordinary skill in the relevant art.

For brevity, upper and lower limitations on physical properties and process conditions may be expressed as ranges. However, it is to be understood that such ranges may comprise any combination of those upper and lower limits recited in any combination herein for a particular component, compound, composition, and/or process. While embodiments may be expressed as comprising a particular limitation, it is to be understood for use herein that such compositions may also consist of and/or consist essentially of the same limitations referred to herein as comprising a particular limitation.

Broadly, the present invention generally provides a cation exchange capacity titration unit and a method of determining the cation exchange capacity of a sample.

Figure 1:
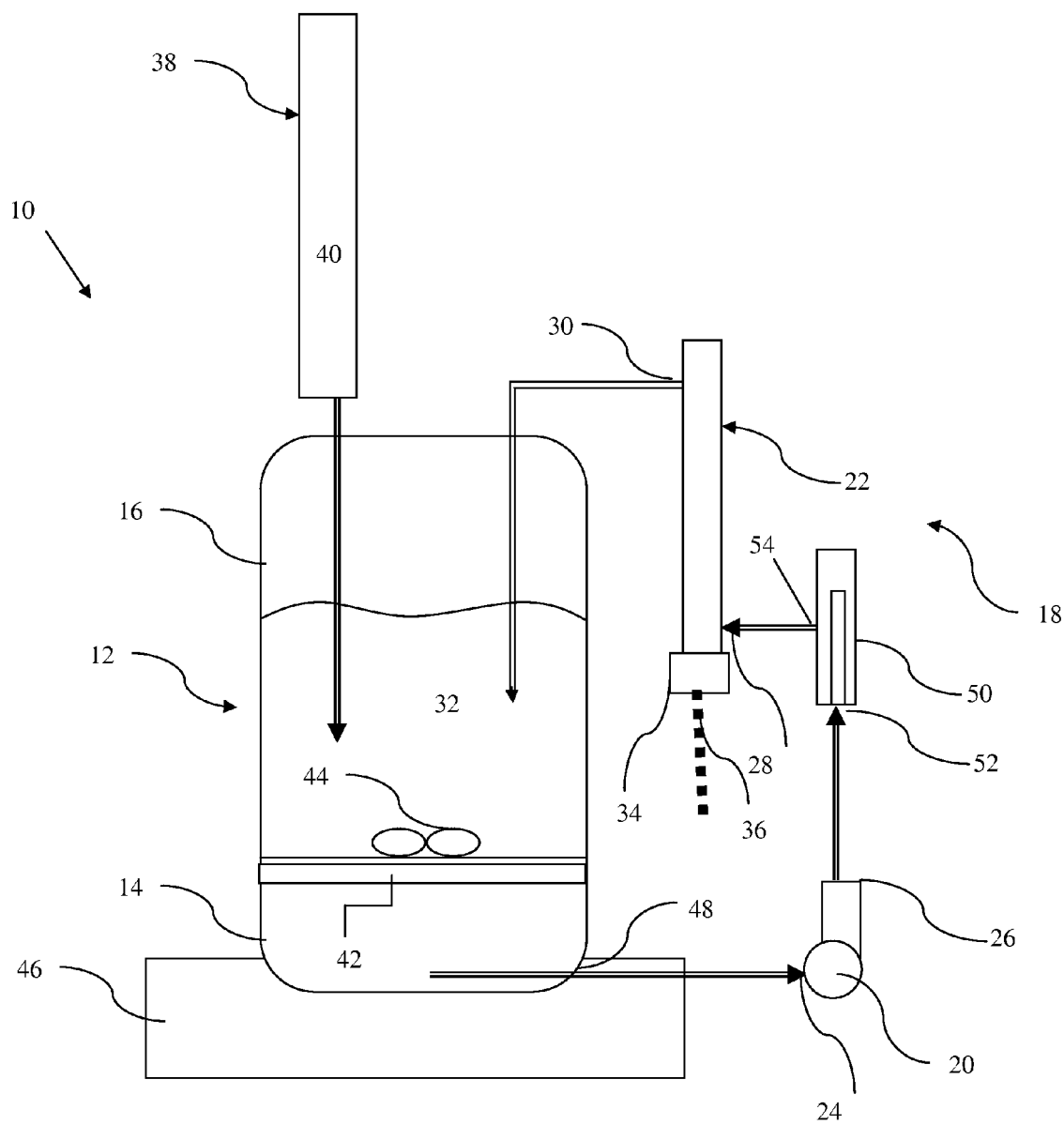
FIG. 1 is a block diagram of an embodiment of the present invention.

Refer now to the drawings wherein depicted elements are not necessarily shown to scale and wherein like or similar elements are designated by the same reference numeral through the several views. FIG. 1 depicts, in block diagram form, an embodiment of the cation exchange capacity titration unit, generally referred to as 10. The titration unit 10 includes a titration cell 12 having a closed bottom end 14 in fluid communication with an open top end 16.

Titration Cell 12 further includes a recirculation loop 18 comprising a pump 20 and a sensing unit 22, wherein pump 20 comprises a pump inlet 24 in fluid communication with bottom end 14 of titration cell 12 through a bottom end outlet 48. Pump 20 also includes a pump outlet 26 in fluid communication with a sensing unit inlet 28. Sensing unit inlet 28 being in fluid communication with a sensing unit outlet 30, wherein sensing unit outlet 30 is in fluid communication with top end 16 of titration cell 12 such that operation of pump 20 results in liquid analyte sample 32 flowing from bottom end 14 through pump 20, through sensing unit 22, and back into titration cell 12 in a continuous loop.

Sensing unit 22 further comprises a sensing element 34 capable of providing a sensing element output signal 36 proportional to a concentration of an analyte in liquid analyte sample 32. Titration unit 10 further comprises a dispensing burette 38 capable of dispensing a known amount of a titrant 40 into top end 16 of titration cell 12 such that titrant 40 contacts analyte sample fluid 32.

In an embodiment, titration cell 12 may further comprises a filter support 42 located within titration cell 12 between top end 16 and bottom end 14 of titration cell 12 such that top end 16 of titration cell 12 is in fluid communication with bottom end 14 of titration cell 12 through filter support 42.

In another embodiment, titration cell 12 may further comprise a stirring mechanism 44 suitable to provide mixing of liquid analyte sample 32 disposed within titration cell 12. Stirring mechanism 44 may include a magnetic stirring plate 46 stirring a magnetic stirrer as shown in FIG. 1, and/or a mechanical stirrer 68 (see FIG. 2), or the like.

In an embodiment, titration unit 10 may further include a gas bubble removal system 50 arranged between pump outlet 26 and sensing unit input 28. Gas bubble removal system 50 may include a bubble removal inlet 52 dimensioned and arranged to overflow into a bubble removal outlet 54 to allow a gas entrapped within analyte sample fluid 32 entering bubble removal inlet 52 to be separated from the liquid such that the liquid flowing through bubble removal outlet 54 is essentially free of entrapped gas bubbles.

Figure 2:
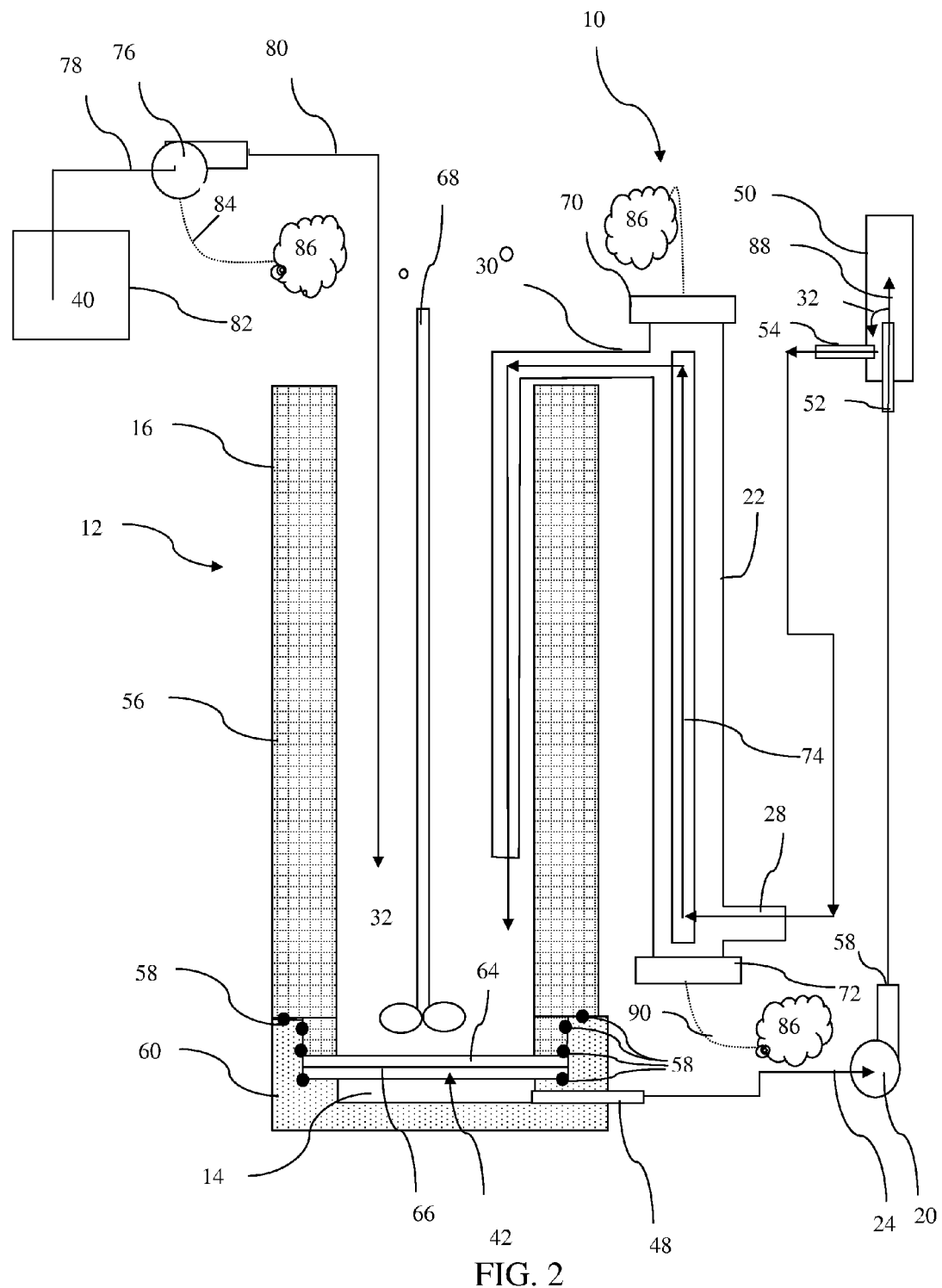
FIG. 2 is a block diagram of an alternative embodiment of the present invention.

Turning now to FIG. 2, in an embodiment, titration cell 12 may comprise a body member 56 comprising top end 16 separated from a mating end 58. Mating end 58 being dimensioned and arranged to sealingly engage a base member 60, wherein base member 60 comprises bottom end 14 of titration cell 12.

In an embodiment, titration cell 12 may further comprise filter support 42 disposed between mating end 58 of body member 56 and base member 60. Base member 60 comprises bottom end outlet 48 in proximity to bottom end 14 and arranged such that bottom end outlet 48 is in fluid communication with bottom end 14 and pump inlet 24. In this embodiment, bottom end 14 is in fluid communication with top end 16 through filter support 42.

As shown in FIG. 2, body member 56 may sealingly engage base member 60 via one or more o-ring seal(s) 58, and/or body member 56 may threadedly engage and/or frictionally engage base member 60. In an embodiment, filter support 42 may comprise a semi-permeable membrane 64 (e.g., filter paper) supported on a permeable rigid support member (e.g., a screen, a fitted disk, and/or the like.) Filter support 42 and/or semi-permeable membrane 64 may sealing engage base member 60 and/or filter support 42 via one or more o-ring seal(s) 58, and/or the like.

In an embodiment, sensing unit 22 may comprise an electromagnetic radiation source 70 separated from an electromagnetic radiation sensor 72 along a sample flow path 74 disposed between sensing unit inlet 28 and the sensing unit outlet 30. In an embodiment, sensing unit inlet 28 and/or sensing unit outlet 30 are arranged perpendicular to sample flow path 74.

In an embodiment, electromagnetic radiation source 70 may include a laser and electromagnetic radiation sensor 72 may include an optical sensor, both of which are tuned to a peak absorption indicative of titrant 40.

In an embodiment, gas bubble removal system 50 comprises bubble removal inlet 52 arranged above bubble removal outlet 54 such that gas bubbles 88 are separated from analyte sample fluid 32 flowing into gas bubble removal system 50 allowing analyte sample 32 to flow out of bubble removal outlet 54 essentially free from gas bubbles.

In an embodiment, the dispensing burette may comprise a metering pump 76 having a metering pump inlet 78 in fluid communication with a titrant reservoir 82, and a dispending outlet 80 in fluid communication with top end 16 of titration cell 12. In an embodiment, metering pump 76 is capable of dispensing a known amount of a titrant 40 from titrant reservoir 82 into titration cell 12, preferably in response to a metering pump output signal 84 from a computer control system 86.

Computer control system 86 may include a central processor, a data storage system, an operator interface, and/or a data manipulation system, as a single unit or as a plurality of separate interconnected units, represented collectively herein as 86, and may comprise a sensor input 90 in electronic communication with sensing unit 22, metering pump output 84 in electronic communication with metering pump 76, wherein computer control system 86 is capable of transferring inputs and/or outputs to and from computer control system 86 to sensing unit 22 and/or metering pump 76, and wherein computer control system 86 is capable of accepting input from and displaying information to an operations technician (not shown), to determine the cation exchange capacity of an analyte sample.

In an embodiment, a method of determining the cation exchange capacity of a sample utilizing the cation exchange capacity titration unit described herein may comprise the steps of:

disposing an amount of a sample into titration cell 12 of cation exchange capacity titration unit 10;

diluting the sample with a known volume of water to produce analyte sample 32;

engaging pump 20 such that analyte sample 32 circulates in recirculation loop 18 from bottom end 14 of titration cell 12 back into top end 16 of titration cell 12;

titrating analyte sample 32 by contacting analyte sample 32 with portions of titrant 40 in titration cell 12 utilizing dispensing burette 38 or metering pump 76 and recording sensing element output signal 36 of sensing element 34 (or sensor output 90 of electromagnetic radiation sensor 72) in response to the concentration of titrate 40 in analyte sample 32 via the metered addition of the titrant 40, until an end point in the titration is reached.

In an embodiment, the titrant comprises methylene blue, (CAS No. 61-73-4); preferably at 3.2 g/l such that 1 ml of the titrant has 0.01 milliequivalents of the indicator.

Sample preparation prior to titration may be consistent with API 13B-1 (ISO 10414-1) or equivalent. However, the instant titration unit may be modified and/or appended to titrate other types of samples and/or to determine other characteristics of a variety of sample materials.

EXAMPLES

Accuracy Determination

A titration unit according to FIG. 2 was assembled. The sensing unit included a laser source coupled with an optical detector in electronic communication with a computer data acquisition and control system running software (DAQ.) A peristaltic pump was utilized in the recirculation loop, and agitation of the sample in the titration cell was accomplished utilizing a magnetic stirrer. The titrant was dosed into the titration cell utilizing a computer controlled metering pump in electronic communication with the DAQ. The samples were prepared according to API 13B-1, using water as the diluent. 6 separate samples were split each into two portions and titrated in duplicate, with the first portion of the sample being hand titrated according to API 13B-1, and the second portion of the sample being titrated utilizing the instant titration unit under computer control.

Precision Determination

In other testing, a single sample was split into 8 separate samples and four of the samples were hand titrated according to API 13B-1, and the other four samples were titrated utilizing the instant titration unit under computer control. The results are shown in Table 1.

TABLE 1

| Sample No. | Comparative API 13B-1 Hand Titration Cation Exchange Capacity BE (kg/m$^3$) | Inventive Modified API 13B-1 Computer Controlled Cation Exchange Capacity BE (kg/m$^3$) |
|---|---|---|
| Accuracy Determination | | |
| 1 | 4 | 4.17 |
| 2 | 13 | 13.00 |
| 3 | 18 | 18.24 |
| 4 | 12 | 11.92 |
| 5 | 24 | 23.84 |
| 6 | 14 | 13.84 |
| Precision Determination | | |
| 7a | 14 | 14.09 |
| 7b | 14 | 14.09 |
| 7c | 14 | 14.09 |
| 7d | 14 | 13.89 |

As the data clearly shows, the instant titration unit and method is both accurate and precise as compared to the standard "hand titration" method of API 13B-1.

It should be understood, of course, that the foregoing relates to preferred embodiments of the invention and that modifications may be made without departing from the spirit and scope of the invention as set forth in the following claims.

What is claimed:

1. A cation exchange capacity titration unit comprising:
a titration cell, a metering pump, and a computer control system;
the titration cell having a closed bottom end in fluid communication with an open top end;
a recirculation loop capable of circulating a liquid analyte sample from the bottom end of the titration cell back into the top end of the titration cell,
the recirculation loop comprising a pump and a sensing unit, wherein the pump comprises a pump inlet in fluid communication with the bottom end of the titration cell, and a pump outlet in fluid communication with a sensing unit inlet, the sensing unit inlet being in fluid communication with a sensing unit outlet, wherein the sensing unit outlet is in fluid communication with the top end of the titration cell; the sensing unit further comprising a sensing element capable of providing an electric signal proportional to a concentration of an analyte in the liquid analyte sample;
the metering pump having an inlet in fluid communication with a titrant reservoir, and a dispending outlet in fluid communication with the top end of the titration cell, wherein the metering pump is capable of dispensing a known amount of a titrant from the titrant reservoir into the titration cell in response to an output from the computer control system;
the computer control system comprising comprises a sensor input in electronic communication with the sensing unit a metering pump output in electronic communication with the metering pump, a central processor, a data storage system, and an operator interface, and a data manipulation system, wherein the computer control system is capable of transferring inputs and/or outputs to and from the computer control system to the sensing unit and/or the metering pump, and wherein the computer control system is capable of accepting input from and displaying information to an operations technician, to determine the cation exchange capacity of a sample; and
a filter support located within the titration cell between the too end and the bottom end of the titration cell, the too end of the titration cell in fluid communication with the bottom end of the titration cell through the filter support the bottom end outlet located below the filter support.

2. The cation exchange capacity titration unit of claim 1, wherein the titration cell further comprises a stirring mechanism suitable to provide mixing of the titrant and the analyte sample disposed within the titration cell.

3. The cation exchange capacity titration unit of claim 1, wherein the titration cell comprises a body member comprising the top end separated from an inner mating end, the mating end being dimensioned and arranged to sealingly engage a base member, the titration cell further comprising a filter support disposed between the mating end of the body member and the base member;

wherein the base member comprises a sample outlet in proximity to the bottom end, wherein the sample outlet is in fluid communication with the top end through the filter support, and wherein the sample outlet is in fluid communication with the pump inlet.

4. The cation exchange capacity titration unit of claim 3, wherein the filter support comprises a semi-permeable membrane supported on a rigid support member.

5. The cation exchange capacity titration unit of claim 1, wherein the sensing unit comprises an electromagnetic radiation source separated from an electromagnetic radiation sensor along a sample flow path disposed between the sensing unit input and the sensing unit output; wherein the sensing unit input and/or the sensing unit output are arranged perpendicular to the sample flow path.

6. The cation exchange capacity titration unit of claim 1, further comprising a gas bubble removal system arranged between the pump outlet and the sensing unit input, the gas bubble removal system comprising a bubble removal inlet which overflows into a bubble removal outlet to allow a gas entrapped within a liquid entering the bubble removal inlet to be separated from the liquid such that the liquid flowing through the bubble removal outlet is essentially free of entrapped gas.

* * * * *